United States Patent [19]
Spira et al.

[11] Patent Number: 5,925,739
[45] Date of Patent: Jul. 20, 1999

[54] PHARMACEUTICAL FORMULATION FOR SUBCUTANEOUS INTRAMUSCULAR OR INTRADERMAL ADMINISTRATION OF FACTOR VIII

[75] Inventors: Jack Spira, Stockholm; Lars Widlund, Spånga; Thomas Österberg, Stockholm; Brita Sjöström, Saltsjö-Duvnäs; Marianne Mikaelsson, Bromma, all of Sweden

[73] Assignee: Pharmacia & Upjohn AB, Stockholm, Sweden

[21] Appl. No.: 08/716,140

[22] PCT Filed: Mar. 31, 1995

[86] PCT No.: PCT/SE95/00348

§ 371 Date: Sep. 17, 1996

§ 102(e) Date: Sep. 17, 1996

[87] PCT Pub. No.: WO95/26750

PCT Pub. Date: Oct. 12, 1995

[30] Foreign Application Priority Data

Mar. 31, 1994 [SE] Sweden .................................. 9401105
Jan. 5, 1995 [SE] Sweden .................................. 9500036

[51] Int. Cl.$^6$ .................................................. A61K 35/14
[52] U.S. Cl. ........................... 530/383; 530/384; 514/12; 424/94.63; 424/94.3; 435/212; 435/69.1
[58] Field of Search ............................... 424/94.63, 94.3; 435/212, 69.1; 530/384, 383; 514/12

[56] References Cited

U.S. PATENT DOCUMENTS

| | | | |
|---|---|---|---|
| 4,749,780 | 6/1988 | Andersson et al. | 530/383 |
| 4,877,614 | 10/1989 | Andersson et al. | 424/101 |
| 5,328,694 | 7/1994 | Schwinn | 424/423 |
| 5,399,670 | 3/1995 | Bhattacharya et al. | 530/383 |
| 5,576,194 | 11/1996 | Chan | 435/69.6 |
| 5,618,789 | 4/1997 | Capon et al. | 514/12 |
| 5,633,150 | 5/1997 | Wood et al. | 435/69.6 |

FOREIGN PATENT DOCUMENTS

| | | |
|---|---|---|
| 0160457 | 11/1985 | European Pat. Off. . |
| 0197901 | 10/1986 | European Pat. Off. . |
| 0522491 | 1/1992 | European Pat. Off. . |
| 56-127308 | 10/1981 | Japan . |
| WO9201440 | 2/1991 | WIPO . |
| WO9109122 | 6/1991 | WIPO . |
| WO9307890 | 4/1992 | WIPO . |
| WO 94/07510 | 10/1993 | WIPO . |
| WO9324137 | 12/1993 | WIPO . |
| WO9501804 | 1/1994 | WIPO . |
| WO 94/26286 | 11/1994 | WIPO . |
| WO9426286 | 11/1994 | WIPO . |

OTHER PUBLICATIONS

Kakizaki (1988) Patent Abstracts of Japan, vol. 12, No. 283, C–518, abstract of Japan, A, 63–63624.
Japanese Patent Abstract JP 56127308, Dialog Information Services, file 351, WPI, Dioalog Accession No. 003224052, WPI Accession No. 81–846100/46, Green Cross Corp. of Japan (1981).
Andersson et al. (1986) Proc. Natl. Acad. Sci. USA vol. 83, pp. 2979–2983.
Johnson et al. (1971) British J. of Hematology, vol. 21, pp. 21–41.
Wang et al. (1988) J. Parenteral Science and Tech. vol. 42, Supplement, pp. S3–S26.
International Search Report for PCT/SE95/00348 completed Jun. 30, 1995.
Patent Abstracts of Japan, vol. 12, No. 283, C–518, abstract of Japan, A, 63–63624 (Estuko Kakizaki), Mar. 22, 1988.
Medical Intelligence—Pool et al, vol. 275, No. 10, Sep. 1966, J.G. Pool et al *Ineffectiveness of Intramuscularly Injected Factor VIII Concentrate in Two Hemophilic Patients*, pp. 547–548.
Arzneim.—Forsch./Drug Res., vol. 39(1), No. 4, 1989, A. Conte, L. Palmieri et al, *Absorption and Excretion in the Experimental Animal of a 14c–Ethylmaleimide Labelled Peptide Fraction of Bovine Factor VIII with Antihaemorrahigc Activity*, pp. 463–466.
Dialog Information Services, file 351, WPI, Dialog accession No. 003224052, WPI accession No. 81–846100/46, Green Cross Corp., of Japan No. 56–127308, Oct. 6, 1981.
Nature, vol. 312, *Expression of active human VIII from recombinant DNA Clones*, William I Wood, et al., Nov. 22, 1984, pp. 330–337.
Proc. Natl. Acad. Sci. USA, vol. 83, *Medical Sciences Isolation and characterization of human factor VIII: Molecular forms in commercial factor VIII concentrate, cyroprecipitate, and plasma*, Andersson, et al., pp. 2979–2983 (1986).
Journal of Pharmaceutical Sciences, vol. 63, No. 1, Jan. 1974, *CMC of Polysorbates*, Lucy S. C. Wan and Phillip F. S. lee, pp. 136–137.
British journal of Haematology, 1971, 21, 21, *Clinical Investigation of Intermediate–and High–Purity Antihaemophilic Factor (Factor VIII) Concentrates*, A. J. Johnson, et al., pp. 21–41.
Hemophilia 1994, Nilsson, et al., pp. 2 and 3.
American Journal of Hematology 1994, vol. 47, No. 1 *Subcutaneous Faxtor IX Administration to Patients with Hemophilia B*, Mauro Berrettini, et al.

*Primary Examiner*—Charles L. Patterson, Jr.
*Assistant Examiner*—Enrique D. Longton
*Attorney, Agent, or Firm*—Dinsmore & Shohl LLP

[57] ABSTRACT

The present invention relates to a pharmaceutical formulation for subcutaneous, intramuscular or intradermal administration comprising coagulation factor VIII or factor IX and use thereof for manufacture of a medicament for treating haemophilia A or B. The formulation comprises coagulation factor VIII or factor IX with an activity of at least 200 IU/ml and an additive increasing the bio-availability of factor VIII or factor IX. Tests with factor VIII gives a therapeutic level of active factor VIII in the blood stream for a surprisingly long period of time after subcutaneous, intramuscular or intradermal administration. The factor VIII is suitably a highly purified recombinant factor VII, and preferably a deletion derivative thereof, which can be used for the manufacture of a medicament for subcutaneous administration.

30 Claims, No Drawings

PHARMACEUTICAL FORMULATION FOR SUBCUTANEOUS INTRAMUSCULAR OR INTRADERMAL ADMINISTRATION OF FACTOR VIII

This is a national stage application of PCT/SE95/00348 filed Mar. 31, 1995 and claims benefit of Swedish applications 9401105-3 filed Mar. 31, 1994 and 9500036-0 filed Jan. 5, 1995.

FIELD OF THE INVENTION

The present invention relates to a pharmaceutical formulation for subcutaneous intramuscular or intradermal administration comprising coagulation factor VIII or factor IX and use thereof for manufacture of a medicament for treating haemophilia A or B. The formulation comprises coagulation factor VIII or factor IX with an activity of at least 200 IU/ml and an additive increasing the bioavailability of factor VIII or factor IX. Tests with factor VII gives a therapeutic level of active factor VIII in the blood stream for a surprisingly long period of time after subcutaneous, intramuscular or intradermal administration. The factor VIII is suitably a highly purified recombinant factor VIII, and preferably a deletion derivative thereof, which can be used for the manufacture of a medicament for subcutaneous administration.

BACKGROUND OF THE INVENTION

Haemophilia is an inherited disease which has been known for centuries but it is only within the last four decades that it has been possible to differentiate between the various forms; haemophilia A, haemophilia B and haemophilia C. Haemophilia A is the most frequent form. It affects only males with an incidence of one or two individuals per 10,000 live-born males. The disease is caused by strongly decreased level or absence of biologically active coagulation factor VIII (antihaemophilic factor), which is a protein normally present in plasma. The clinical manifestation of haemophilia A is a strong bleeding tendency and before treatment with factor VIII concentrates was introduced, the mean age of those patients was less than 20 years. Concentrates of factor VIII obtained from plasma have been available for about three decades. This has improved the situation for treatment of haemophilia patients considerably and given them possibility to live a normal life.

It is commonly recognized that the severity of haemophilia A and B, can be divided into three categories: severe, moderate and mild. In severe haemophilia A, the plasma level of factor VIII activity in the blood is less than 1% of the normal plasma level. In moderate haemophilia A, the plasma level of factor VIII activity in the blood is in the range of from 1 up to 4% of the normal plasma Level. In mild haemophilia A, the plasma level of factor VIII activity in the blood is in the range of from 5 up to 25% of the normal plasma level. The normal plasma level of factor VIII activity in the blood is defined as 1 IU/ml of blood Severe, moderate and mild haemophilia B, are defined by the same plasma levels as those given for factor VIII above. The normal plasma level of factor IX activity in the blood is defined as 1 IU/ml of blood Reference is here made to Inga Marie Nilsson in Hemophilia, Pharmacia Plasma Products, Stockholm, Sweden, p. 2–3, 1994.

A medicament with a very large and labile molecule, such as coagulation VIII with a molecular mass of 170 to 300 kDa, is normally given intravenously since these medicaments normally exhibit a very low bioavailability due to insufficient absorption and severe degradation, if given subcutaneously, intramuscularly or intradermally. Thus, a factor VIII concentrate dissolved in sodium citrate and injected intramuscularly yielded a maximum circulating level of only 1.4% of the normal plasma level (Pool et al, New England J. Medicine, vol. 275, no. 10, p. 547–548, 1966). The studies further revealed that there was no significant difference in the activity recovered in the circulation regardless of whether such citrate was added to the preparation. In a later study, a high-purity factor VIII was administered intramuscularly to haemophilic dogs and human volunteers (Johnson et al, Br. J. Hematology, vol. 21, p. 21–41, 1971). Although, the doses were much larger than used by Pool et al, neither the dogs nor the human volunteers showed a significant rise in plasma factor VIII levels. In fact, the plasma factor VIII concentration in the haemophilic human volunteers remained below 1% of the normal plasma level, i.e. the severe haemophilia A prevailed even after administration in the absence of additives increasing the bioavailability.

Various additives have been proposed for enhancing the absorption of a great number of pharmaceuticals, including small molecules such as insulin and peptide fractions of factor VIII. Thus, WO-A-92/01440 relates to use of dimethyl-$\beta$-cyclodextrin for enhancing transmucosal administration of insulin with a molecular mass of about 5,800 Da. Information pertaining to transport of small molecules by non-invasive routes, cannot be transferred to transport of large molecules to the intravenous circulation by subcutaneous, intramuscular or intradermal administration. This is especially true, since the aim of WO-A-92/01440 is to make superfluous injections of (poly)peptides or proteins. Furthermore, before intramuscular administration saline is used for dissolving peptide fractions of factor VIII with a molecular mass of from 1,000 to 20,000 Da (Conte et al, Arzneim.-Forsch./Drug Res., vol. 39 (I), no. 4, p. 463–466, 1989). Here, also, the experiments relate to small molecules yielding an unknown bioavailability since the activity of the peptide fractions of factor VIII has not been determined.

EP-A-0 522 491 relates to use of a water-soluble species of hyaluronic acid in combination with a water-soluble protein showing no substantial pharmacological activity for enhancing administration of a pharmacologically active polypeptide. Blood clotting factors are mentioned amongst a great number of polypeptides. Furthermore, there are no examples showing the possible effect of hyaluronic acids upon a administration of any blood clotting factor e.g. by injection JP-A-63-063624 relates to use of collagen for providing slow release of an unspecified drug upon e.g. subcutaneous administration.

JP-A-56-127308 relates to emulsions containing blood-coagulation factor VIII, soybean oil and phospholipids. The object of these emulsions is to eliminate the problems encountered with conventional parenteral administration. The emulsions are therefore administered orally, which is shown in several of the examples.

Factor VIII can also be used for other therapeutic purposes than for treating haemophilia A. Thus, WO-A-93/24137 relates to formulations Factor VIII intended for intradermal or topical administration as an antiinflammatory agent. The formulations are intended for local administration to non-haemophilic human bodies and not to the intravenous circulation of humans suffering from haemophilia A. The therapeutic effect is thus local and not systemic, the latter being required to alleviate haemophilia A.

Subcutaneous administration of factor VIII without additives is known from Berett et al, Am. J. Hematology, vol 47, no. 1, p. 61–62, 1994. Factor IX is a smaller molecule than factor VIII having a molecular mass of about 56 kDa. The human factor IX was poorly and very slowly transported into the circulation, when injected into the subcutaneous tissue of hemophilia B patients. This is in agreement with the results obtained with factor VIII.

The presently available factor VIII and factor IX preparations on the market are made as a formulation for intravenous administration and the majority of the factor VIII preparations are stabilized with human serum albium.

Large and viable proteins are thus normally given intravenously so that the medicament is directly available in the blood stream. It would however be advantageous if a medicament could be given subcutaneously, intramuscularly or intradermally as these administration forms are much easier to handle for the patient. Especially if the medicament must be taken regularly during the whole life and treatment is to start early, already during the patients first year of life.

DESCRIPTION OF THE INVENTION

To our great surprise we have found that factor VIII which is a very sensitive to proteins can be given subcutaneously and, in contrast to all earlier experience we obtain a readable absorption and a surprisingly high level of active factor VIII protein in the blood.

We have thus developed a formulation which makes it possible to administer factor VIII subcutaneously, intramuscularly or intradermally and which gives a great advantage for all patients in need of factor VIII.

Recombinant factor VIII SQ is indicated for treatment of classical haemophilia. The half-life for r-VIII SQ is approximately 12 hours for humans when injected intravenously. For prophylactic treatment 15–40 IU/kg bodyweight is given of factor VIII three times a week.

An intravenous injection is normally 5–20 ml. An injection given subcutaneously is between 0.05 to 1 ml and the concentration of factor VIII must therefore be very high in such a formulation. This is possible to obtain e.g. with our highly purified recombinant factor VIII in a formulation with an additive such as a hydrolyzed gelatin, hyaluronic acid and/or soybean oil emulsion. Thus, with the present invention it may be possible to obtain a bioavailability of at least about 15%, suitably at least about 30%, after subcutaneous, intramuscular or intradermal administration, compared to the bioavailability obtained after intravenous administration. With an especially careful selection of the constituents of the formulation of the present invention, it is possible to obtain a bioavailability of at least 50% and even 70% after subcutaneous, intramuscular or intradermal administration, compared to the bioavailability obtained after intravenous administration.

The inventive idea is thus a combination of the finding that factor VIII can be absorbed into the blood-stream when given as a subcutaneous, intramuscular or intradermal pharmaceutical formulation and that it is possible to produce a special formulation giving the required increase in bioavailability of factor VIII for this purpose.

The present invention thus relates to a pharmaceutical formulation for subcutaneous, intramuscular or intradermal administration comprising coagulation factor VIII or factor IX with an activity of at least 200 IU/ml and an additive increasing the bioavailability of factor VIII or factor IX, which formulation gives a therapeutic level of factor VIII or factor IX activity of at least 1.5% of the norm plasma level in the blood for at least 6 hours after administration.

A therapeutic level in the present invention, relates to at least 1.5% of the normal plasma level of factor VIII or factor IX activity in the blood. The factor VIII or factor IX activity in the blood is suitably 2.5% of the normal plasma level, and preferably at least 4%.

With the formulations of the present invention, it is possible to maintain a therapeutically acceptable level of VII:C or IX:C for at least 6 hours, suitably more than 12 hours, preferably more than 24 hours, and more preferably more than 48 hours,. With optimized formulations it is probably possible to maintain a therapeutically acceptable level of VIII:C or IX:C for at least 96 hours, and even more than 168 hours In this way, the frequency of administration can be kept to a minimum, while still giving the intended therapeutic effect. The formulations according to the invention may also be suitable for on-demand treatment.

The present invention relates to treatment of haemophilia A or B, diseases which, if present, prevails in the entire blood system. Thus, a prerequisite for succesful treatment is administration in such a way, that a systemic effect is obtained. Such a systemic effect is obtained by the present invention, as opposed to other techniques, where local, e.g. anti-inflammatory effects are desired.

The formulation containing factor VIII or IX, are preferably given subcutaneously.

The factor VIII activity in the formulation is at least 200 IU/ml, suitably more than 500 and preferably more than 1,000 IU/ml. It is particularly preferred that the factor VIII activity is more than 1,500 IU/ml in the formulation and most particularly preferred that the activity is from 5,000 to 100,000 IU/ml.

The volume given can be more than 0.01 ml, stably 0.1 to 2 ml, preferably 0.25 to 1.5 ml, and more preferably 0.5 to 1 ml. The volume can also be 0.1 to 1 ml.

The activities and volumes given above, are equally applicable to factor IX.

Factor VIII and factor IX can either be plasma derived or produced by recombinant DNA techniques.

While the invention is applicable to both coagulation factor VIII and factor IX, it will in the following be described in more detail with reference to factor VIII.

Therapeutic factor VIII concentrates have until now been prepared by fractionation of plasma. However, there are now methods available for production of factor VIII in cell culture using recombinant DNA techniques as reported in e.g. W. Wood et al., Nature 312, p. 330–37, 1984 and EP-A-160 457.

Factor VIII concentrates derived from human plasma contain several fragmented fully active factor VIII forms (Andersson et al, Proc. Natl. Acad. Sci. U.S.A., Vol 83, p. 2979–83, May 1986). The smallest active form of human factor VIII has a molecular mass of 170 kDa and consists of two chains of 90 kDa and 80 kDa held together by a metal ion bridge. Reference is here made to EP-A-197 901. Pharmacia AB of Sweden has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium.

The structure and biochemistry of recombinant factor VIII products in general have been described by Kaufman in Trends in Biotechnology, Vol 9, 1991 and Hematology, 63, p. 155–65, 1991. The structure and biochemistry of r-VIII SQ has been described in WO-A-91/09122.

When factor VIII is recombinant, it can be either in its full-length form or preferably a deletion derivative thereof. More preferably the deletion derivative is recombinant factor VIII SQ (r-VIII SQ). By deletion derivative is here meant coagulation factor VIII, in which the whole or part of the B-domain is missing. Additionally, the factor VIII molecule, and in particular the r-VIII SQ molecule, can be chemically modified, e.g. by pegylation, covalently linked carbohydrates or polypeptides, in order to improve the stability of the molecule in vivo.

Our used factor VIII is highly purified, i.e. has a specific activity of more than 5,000 IU/mg protein, even more than 12,000 IU/mg and is preferably stabilized without the addition of albumin.

Additives increasing the bioavailability of factor VIII are suitably organic compounds per se, salts thereof, emulsions or dispersions containing organic compounds per se or salts thereof, e.g. dispersions of polar lipids, or any combination or sequence of addition thereof. Organic compounds per se useful in the present invention are e.g. amino acids, peptides, proteins, and polysaccharides. Peptides include dipeptides, tripeptides, oligopeptides and polypeptides, such as collagen and gelatin. The collagen and gelatin are preferably hydrolyzed. Polysaccharides include e.g. chitosans, cyclodextrins, starch, hyaluronic acids, dextrans, cellulose, and any derivatives, combinations and/or sequence of addition thereof. The starch is preferably hydrolyzed. The emulsions include oil-in-water emulsions with oil as the dispersed phase and water-in-oil emulsions with oil as the continuous phase. The oil can be of vegetable or origin or synthetically produced. Suitably, the vegetable oil of the emulsions is soybean oil or safflower oil, or any combination thereof. A preferred emulsion is Intralipid® sold by Pharmacia AB of Stockholm, Sweden, which further contains egg lecithin. Suitably, the polar lipids are one or more phospholipids or glycolipids or any combination thereof. Preferably, the hyaluronic acid is Healon® sold by Pharmacia AB of Uppsala, Sweden. Preferably, the dextran is Promiten® sold by Pharmacia AB of Uppsala, Sweden.

The additives increasing the bioavailability of factor VIII could be added to the formulation before drying or upon reconstitution, or it could be added to a stable solution or dispersion containing factor VIII. A combination of at least two of the additives mentioned could also be added. Furthermore, two or more of the additives mentioned could be added in a sequence.

One or more anticoagulants can also be added to the formulation, in a non-therapeutic amount. The anticoagulants can be e.g. glucosaminoglycans such as heparins, heparin fragments, heparin derivatives, or heparan sulphate. A preferred group of glucosaminoglycans is the low molecular weight heparins (LMWH) with an average molecular mass of up to about 10,000 Da, more preferably from 2,000 up to 8,000 Da.

Before administration, one or more aqueous solutions or dispersions could be added, in any mixture or sequence, to a formulation according to the present invention, which is a stable aqueous solution, a dispersion or in dried form.

The formulation can also comprise sodium or potassium chloride, preferably in an amount of more than 0.1M.

The association of the heavy and light chains of factor VIII, is dependent on the presence of calcium (or other divalent metal ions). Here, calcium was added as calcium chloride ($CaCl_2$) but other salts such as calcium gluconate, calcium glubionate or calcium gluceptate can also be used, preferably in an amount of more than 0.5 mM.

An amino acid is preferably used to buffer the system and it also protects the protein in the amorphous phase if the formulation is freeze-dried. A suitable buffer could be L-histidine, lysine and/or arginine. L-Histidine has primarily been chosen because of the good buffer capacity of L-histidine around pH 7.

A non-ionic surfactant can also be present in the formulation and is then preferably chosen from block co-polymers, such as a poloxamer or polyoxyethylene sorbitan fatty acid ester, such as polyoxyethylene(20) -sorbitan monolaurate or polyoxyethylene-(20)-sorbitan monooleate The non-ionic surfactant, if used, should preferably be present in an amount above the critical micelle concentration (CMC). See Wan and Lee, Journal of Pharm Sci, 63, p136, 1974. The polyoxyethylene sorbitan fatty acid ester is preferably used in an amount of at least 0.01 mg/ml.

To this formulation monosaccharide disaccharides or sugar alcohols, preferably sucrose, could be added. Also antioxidants such as gluthatione, acetylcystein, tocopherol, methionine, butyl hydroxy toluene and/or butyl hydroxy anisole could be added.

Complexing agents, such as EDTA and citric acid, can also be present in small concentrations for stabilizing the factor VIII molecules, if they exhibit a stronger affinity for destabilizing metal ions than for calcium or other divalent metal ions associating the chains of factor VIII. Furthermore, preservatives such as benzyl alcohol, phenol, sorbic acid, parabens and chlorocresol could be added.

The formulation comprises preferably L-histidine and sucrose. The ratio of sodium chloride to L-histidine and sucrose in the composition for freeze-drying is suitably more than 1:1 (w:w), preferably more than 2:1 (w:w).

The formulation could comprise i) at least 200 IU/ml of factor VIII, preferably at least 1,500 IU/ml of a deletion derivative of recombinant factor VIII ii) at least 0.01 mg/ml of a polyoxyethylene sorbitan fatty acid ester iii) sodium chloride, preferably in an amount of more than 0M.

iv) calcium salt, such as calcium chloride or calcium gluconate, preferably in an amount of more than 0.5 mM v) an amino acid such as L-histidine in an amount of more than 1 mM.

vi) an additive increasing the bioavailability of factor VIII.

The formulation could be in a dried form, preferably freeze-dried. Before administration, the dried product can be reconstituted with an aqueous solution or a dispersion, e.g. a suspension, a liposomal formulation or an emulsion.

The claimed formulation can also be a stable aqueous solution ready for administration. It can also be a dispersion, e.g. a suspension, a liposomal formulation or an emulsion.

The formulation could be stored in an oxygen-reduced environment as disclosed in the copending patent-application WO-A-94/26286.

The invention also relates to the use of the claimed formulation for the manufacture of a medicament for subcutaneous, intramuscular or intradermal administration for treating haemophilia, preferably for the use of a deletion derivative of recombinant factor VIII for the manufacture of a medicament for subcutaneous administration. The medicament can be in a stable aqueous solution or dispersion, or dried. It also relates to a method for treatment of haemophilia by subcutaneous, intramuscular or intradermal administration of the claimed formulation.

The data presented in the examples indicate that factor VIII, and in particular r-VIII SQ can be injected subcutaneously and recovered in an active form intravenously in-vivo This is a very surprising finding, as no such formulation has been known earlier.

The protection is not limited to a composition under these examples.

Experimental

Materials and methods

The production of recombinant factor VIII SQ (r-VIII SQ) was essentially performed as described in patent WO-A-91/09122, example 1–3. A DHFR deficient CHO cellline (DG44N.Y.) was electroporated with an expression vector containing the R-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for factor VIII activity A production clone was chosen and sis was subsequently adapted to serum free suspension growth in a defined medium and finally a large scale fermentation process was developed. Supernantant is collected after certain time periods and further purified as described below.

The clarified conditioned medium was pH adjusted and applied to a S-Sepharose FF column. After washing, factor VIII was eluated with a salt buffer containing 5 mM $CaCl_2$.

Immunoadsorption was carried out on an immunoaffinity resin where the ligand was a monoclonal antibody (8A4) directed towards the heavy chain of factor VIII. Before loading to the column the S-eluate was treated with 0.3% TNBP and 1% Octoxynol 9. The column was equilibrated, washed and factor VIII was eluated with a buffer containing 0.05M $CaCl_2$ and 50% ethylene glycol.

The mAb-eluate was loaded on a Q-Sepharose FF column equilibrated with the elution buffer in the immunoaffinity step. After washing, factor VIII was eluated with 0.05M L-Histidine, 0.6M sodium chloride, 4 mM calcium chloride and pH 6.8.

The Q-eluate was applied to a gel filtration column (Superdex 200 p.g.). Equilibration and elution was carried out with a buffer containing L-histidine, sodium chloride and calcium chloride. The protein peak was collected and the solution was formulated before freeze-drying.

This material of r-VIII SQ was received from the final purification step. The factor VIII activity and the concentration of the inactive components were adjusted by diluting with an appropriate buffer containing polyethylene glycol (PEG). The solution was then sterile filtered (0.22 $\mu$m), dispensed and freeze-dried.

EXAMPLE 1

Recombinant factor VIII was prepared according to the method described under Experimental.

The freeze-dried composition containing r-VIII SQ was the following per vial, which was reconstituted in 4 ml sterile water for injection:

| Composition per vial: | |
|---|---|
| L-Histidine, mg | 31.0 |
| Sodium chloride, mg | 70.1 |

| Composition per vial: | |
|---|---|
| Calcium chloride.(2 $H_2O$), mg | 2.35 |
| Polyethylene glycol (PEG 4000), mg | 4.0 |
| Polyoxyethylene-(20)-sorbitan monooleate (Tween 80 ®), mg | 1 |
| VIII:C charged, IU/vial | 4,400 |
| VIII:C in reconstituted solution, IU/ml | 1,060 |

Male albino mice weighing about 30 g and of strain NMRI, SPF, were injected subcutaneously in the neck with the reconstituted r-VIII SQ solution. The volume injected at the dose level of 10,000 IU/kg was 9.4 ml/kg and at the higher dose Level 50,000 IU/kg, 5 times larger, 47 ml/kg. In the placebo treatment saline was used, 94 ml/kg. 3–5 minutes before the blood sampling the mice were anaesthetized intra peritoneally with Mebumal® (pentobarbital) vet. 60 mg/ml. The volume injected was 9.4 ml/kg i.e. about 0.3 ml/mouse. Under the anaesthesia 0.45 ml blood was collected from the vena cava in plastic syringes containing 0.05 ml 0.13M sodium citrate. Plasma was then prepared from the collected blood by centrifugation (8,800 g for 7 minutes) and kept frozen in plastic Cryoflex tubes at -70° C. until the time of determination of factor VIII activity.

Results

TABLE 1

VIII:C in plasma from mice receiving r-VIII SQ 10,000 IU/kg body weight subcutaneously.

| Time after administration (hours) | VIII:C (IU/ml) X ± Sd | n number of observations |
|---|---|---|
| 0 | 0.82 ± 0.43 | 12 |
| 0.33 | 1.23 ± 0.41 | 3 |
| 1.0 | 1.38 ± 0.56 | 4 |
| 1.5 | 1.83 ± 0.60 | 12 |
| 2.0 | 1.43 ± 0.91 | 8 |
| 4.0 | 1.34 ± 0.72 | 6 |
| 6.0 | 1.27 ± 0.42 | 4 |
| 8.0 | 1.55 ± 0.80 | 4 |
| 16.0 | 0.62 ± 0.28 | 4 |
| 20.0 | 0.58 ± 0.12 | 3 |
| 24.0 | 0.76 ± 0.53 | 4 |

TABLE 2

VIII:C in plasma from mice receiving r-VIII SQ 10,000 IU/kg body weight intravenously. The number of observations were 6 throughout the tests.

| Time after administration (min) | VIII:C (IU/ml) X |
|---|---|
| 0 | 1.6 |
| 5 | 66.7 |
| 15 | 43.7 |
| 30 | 32.1 |
| 45 | 27.4 |
| 60 | 22.5 |
| 120 | 15.7 |
| 240 | 2.3 |

TABLE 3

Dose - Response in mice receiving r-VIII SQ subcutaneously.
Dose: Dose r-VIII SQ administrated (IU/kg).
Response: VIII:C in plasma (IU/ml) 1.5 hours after subcutaneous administration.

| Dose (IU/kg) | Response (IU/ml) | Response (IU/ml) (baseline adjusted) | n number of obs. |
| --- | --- | --- | --- |
| Blank (baseline) | 0.82 ± 0.43 | — | 12 |
| Saline | 1.21 ± 0.34 | 0.39 | 4 |
| 10,000 | 1.83 ± 0.60 | 1.01 | 12 |
| 50,000 | 2.47 ± 0.60 | 1.65 | 6 |

Results

1. The change of VIII:C in plasma, with time after a subcutaneous dose of r-VIII SQ, 10,000 IU/kg, shows the typical pattern for a drug being absorbed from a subcutaneous depot (see Table 1). The maximum VIII:C level n plasma is seen at about 1.5 hours after administration (see Table 1). The extremely high dosis used in the above tests, were chosen to get an effect that was statistically significant.

2. The absorption of r-VIII SQ from a subcutaneous depot is further verified by the increase in maximum concentration seen when the dose is increased five-fold. No significant effect was observed on the obtained plasma level of VIII:C when the subcutaneous injection volume was changed from 9.4 to 47 m/kg while the dose of r-VIII SQ was kept constant. Furthermore, the VIII:C obtained in plasma was essentially not dependent on the osmolality of the administration solution.

3. The bioavailability of r-VIII SQ after subcutaneous (s.c.) administration in mouse was about 10% of the bioavailability after intravenous (i.v.) administration, The latter being 100 % by definition. In the present tests the dose level s.c. was the same as the dose level i.v. The bioavailability was calculated from the area under the activity (VIII:C)-time curve (AUC) Thus, the bioavailability after subcutaneous administration, can be calculated according to the following equation (for data see Tables 1 and 2):

$$\text{Bioavailability}_{s.c.} = AUC_{s.c.}/AUC_{i.v.} \cdot \text{dose}_{i.v.}/\text{dose}_{s.c.} \qquad (1)$$

EXAMPLE 2

Recombinant factor VIII was prepared according to the method described under Experimental with the following exceptions: (i) the material of r-VIII SQ that was received from the final purification step was diluted with a buffer not containing PEG, (ii) the r-VIII SQ solution was not freeze-dried it was stored at −70° C.

The r-VIII SQ-solution had the following composition:

| Composition per vial: | |
| --- | --- |
| L-Histidine, mg | 7.5 |
| Sucrose, mg | 158 |
| Sodium chloride, mg | 45 |
| Calcium chloride.(2 $H_2O$), mg | 1.25 |
| Polyoxyethylene-(20)-sorbitan monooleate (Tween 80 ®), mg | 0.50 |
| VIII:C charged, IU/vial | 6,070 |
| VIII:C, IU/ml* | 1,130 |

*Diluted r-VIII SQ-solution (1 part of r-VIII SQ-solution + 1 part of water, v:v)

The r-VIII SQ-solution was diluted with sterile water for injection (1 part of r-VIII SQ-solution+1 part of water, v:v) prior to administration when the dose of VIII:C was below 3,000 IU/kg body-weight.

Female cynomolgus monkey (Macaca fascicularis) weighing about 3–3.5 kg were injected with the r-VIII SQ-solution subcutaneously in the dorsal region. Depending on the dose, the volume of injection was varied between approximately 0.2 to 2.0 ml/kg body-weight. Subcutaneous injections with single doses of 250, 2,500 and 5,000 IU/kg were administered. On each sampling occasion 1.8 ml of blood was collected in tubes containing citrate as anticoagulant (0.2 ml). After centrifugation plasma was separated and frozen in aliquots (<−60° C.).

Results

TABLE 4

VIII:C in plasma from monkeys receiving r-VIII SQ, 250 IU/kg, subcutaneously. The VIII:C in the administration solution was about 1,130 IU/ml.

| Monkey No Sampling after inj. (Hours) | 1 VIII:C (IU/ml) | 2 VIII:C (IU/ml) | 3 VIII:C (IU/ml) |
| --- | --- | --- | --- |
| 0 | 2.15 | 1.49 | 1.76 |
| 1 | 2.32 | 1.75 | 1.92 |
| 4 | 2.43 | 1.52 | 1.89 |
| 8 | 2.48 | 1.67 | 1.92 |
| 10 | 2.41 | 1.76 | 2.03 |
| 12 | 2.29 | 1.70 | 2.01 |
| 14 | 2.20 | 1.69 | 2.00 |
| 24 | 1.76 | 1.32 | 1.98 |
| 30 | 2.31 | 1.46 | 1.90 |
| 48 | 2.18 | 1.64 | 1.96 |

TABLE 5

VIII:C in plasma from monkeys receiving r-VIII SQ, 2,500 IU/kg, subcutaneously. The VIII:C in the administration solution was about 1,130 IU/ml.

| Monkey No Sampling after inj. (Hours) | 4a VIII:C (IU/ml) | 5a VIII:C (IU/ml) | 6a VIII:C (IU/ml) |
| --- | --- | --- | --- |
| 0 | 1.85 | 1.43 | 2.18 |
| 1 | 1.96 | 1.82 | 2.72 |
| 4 | 2.70 | 2.22 | 3.14 |
| 8 | 3.19 | 2.60 | 3.37 |
| 10 | 3.19 | 2.81 | 3.46 |
| 12 | 3.06 | 1.56 | 3.02 |
| 14 | 2.56 | 2.42 | 2.85 |
| 24 | 2.34 | 2.12 | 2.75 |
| 30 | 2.20 | 2.01 | 2.55 |
| 48 | 2.02 | 1.83 | 2.38 |

| Monkey No Sampling after inj. (Hours) | 4b VIII:C (IU/ml) | 5b VIII:C (IU/ml) | 6b VIII:C (IU/ml) |
| --- | --- | --- | --- |
| 0 | 1.98 | 1.35 | 2.30 |
| 2 | 2.43 | 1.88 | 3.05 |
| 6 | 3.51 | 2.45 | 3.59 |
| 9 | 3.91 | 2.47 | 4.16 |
| 11 | 3.47 | 2.24 | 3.68 |
| 13 | 3.11 | 2.06 | 3.34 |
| 22 | 2.38 | 1.55 | 2.79 |
| 40 | 2.01 | 1.49 | 2.38 |

TABLE 6

VIII:C in plasma from monkeys receiving r-VIII SQ, 5,000 IU/kg, subcutaneously. The VIII:C in the administration solution was about 2,470 IU/ml.

| Monkey No Sampling after inj. (Hours) | 7 VIII:C (IU/ml) | 8 VIII:C (IU/ml) | 9 VIII:C (IU/ml) |
|---|---|---|---|
| 0 | 2.04 | 1.78 | 1.54 |
| 2 | 2.99 | 2.37 | 2.99 |
| 6 | 4.56 | 3.33 | 5.32 |
| 9 | 4.75 | 3.89 | 5.70 |
| 11 | 4.72 | 3.32 | 5.46 |
| 13 | 4.23 | 3.06 | 4.63 |
| 22 | 3.03 | 2.33 | 3.46 |
| 40 | 2.76 | 1.77 | 2.60 |

TABLE 7

Dose - Response in monkey receiving r-VIII SQ subcutaneously.
Dose: Dose r-VIII SQ administrated (IU/kg bodyweight).
Response: VIII:C in plasma (IU/ml) about 9 hours after administration.

| Dose (IU/kg) | Response (IU/ml) | Response (IU/ml, baseline adj.) | n number of observations |
|---|---|---|---|
| Blank (baseline) | 1.8 ± 0.3 | — | 9 |
| 250 | | 0.37 ± 0.05 | 3 |
| 2,500 | | 1.70 ± 0.06 | 3 |
| 2,500 | | 2.05 ± 0.57 | 3 |
| 5,000 | | 3.4 ± 1.20 | 3 |

TABLE 8

The bioavailability of r-VIII SQ after subcutaneous administration in monkeys. VIII:C in the administration solution was varied between about 1,130 IU/ml to about 2,470 IU/ml. The bioavailability was calculated according to equation 1, from data given in tables 4–6 and corresponding data after intravenous administration.

| Dose (IU/kg bodyweight) | Bioavailability (%) |
|---|---|
| 250 | 11 |
| 250 | 9 |
| 2,500 | 7 |
| 2,500 | 11 |
| 2,500 | 6 |
| 2,500 | 6 |
| 2,500 | 5 |
| 2,500 | 5 |
| 5,000 | 7 |
| 5,000 | 3 |
| 5,000 | 9 |

Results

1. According to the results (tables 4–6) the plasma concentration as a function of time follows the typical pattern for a drug being absorbed after subcutaneous administration. The maximum concentration of VIII:C is seen about 9 hours after administration.

2. The dose-response relationship obtained (table 7), gives a further verification that there is an absorption of VIII:C into the blood stream following a subcutaneous injection.

3. The bioavailability of r-VIII SQ after subcutaneous administration in monkey was about 5–10% (table 8). The bioavailability was essentially independent of the dose of r-VIII SQ.

EXAMPLE 3

Recombinant factor VIII (r-VIII SQ) of both the compositions (examples 1 and 2) mentioned above were used.

Male albino mice weighing about 30 g and of strain NMRI, SPF, were injected subcutaneously in the neck with the r-VIII SQ formulation.

The dose was 10,000 IU/kg ad the injection volume was about 10 ml/kg. 3–5 min before the blood sampling the mice were anaesthetized intra peritoneally with Mebumal® (pentobarbital) vet. 60 mg/ml. The dose volume was about 0.3 ml/mouse. Under anaesthesia 0.45 ml blood was collected from vena cava in plastic syringes containing 0.05 ml sodium citrate (0.13M). Plasma was prepared from the blood by centrifugation (8,800 g for 7 minutes) and thereafter stored in plastic Cryoflex tubes at −70° C. until determination of factor VIII activity.

The r-VIII SQ-solution in combination with different additives increasing the bioavailability of factor VIII (table 9) was administered subcutaneously in mice.

TABLE 9

The additives that were added to the r-VIII SQ-solution prior to subcutaneous administration in mice.

| Additive | Commercial name/ Commercial source | Concentration of additive in the administered r-VIII SQ-solution |
|---|---|---|
| Amino acid mixture | Vamin ®/Pharmacia AB | 4.5 g N/l |
| Dextran | Promiten ®/Pharmacia AB | 150 mg/ml |
| Hyaluronic acid | Healon ®/Pharmacia AB | 5 mg/ml |
| Hydrolyzed collagen | Prionex ®/Pentapharm Ltd | 150 g/l |
| Hydrolyzed gelatin | Haemaccel ®/Hoechst | 17.5–35 g/l |
| Human serum albumin | Albumin/Pharmacia AB | 100–200 g/l |
| Poly (O-2-hydroxy-ethyl) starch | HAES-steril ®/Meda | 50–100 g/l |
| Soybeanoil emulsion | Intralipid ®/Pharmacia AB | 150–200 mg/ml |

Results

TABLE 10

VIII:C in plasma from mice receiving r-VIII SQ-solution containing hydrolyzed gelatin subcutaneously. The VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.83 ± 0.37 | 4 |
| 6 | 2.02 ± 0.43 | 6 |
| 16 | 1.94 ± 0.44 | 9 |
| 24 | 2.00 ± 0.52 | 5 |
| 30 | 1.52 ± 0.41 | 6 |
| 48 | 1.32 ± 0.41 | 6 |

TABLE 11

VIII:C in plasma from mice receiving r-VIII SQ-solution containing soybeanoil emulsion subcutaneously. The VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.41 ± 0.44 | 4 |
| 3.5 | 1.46 ± 0.34 | 5 |
| 6 | 1.48 ± 0.87 | 4 |
| 16 | 1.29 ± 0.25 | 6 |
| 16 | 1.35 ± 0.31 | 3 |
| 30 | 1.92 ± 0.51 | 6 |
| 48 | 1.97 ± 0.29 | 5 |

TABLE 12

VIII:C in plasma from mice receiving r-VIII SQ-solution containing Poly (O-2-hydroxyethyl) starch subcutaneously. The VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.00 ± 0.44 | 5 |
| 3.5 | 1.62 ± 0.19 | 4 |
| 6 | 1.65 ± 0.69 | 6 |
| 16 | 1.62 ± 0.38 | 6 |
| 16 | 1.19 ± 0.40 | 4 |
| 24 | 0.73 ± 0.52 | 4 |
| 30 | 1.33 ± 0.39 | 5 |
| 48 | 1.10 ± 0.38 | 3 |

TABLE 13

VIII:C in plasma from mice receiving r-VIII SQ-solution containing hyaluronic acid subcutaneously. The calculated VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.67 ± 0.42 | 5 |
| 3.5 | 1.33 ± 0.35 | 4 |
| 6 | 1.72 ± 0.61 | 4 |
| 16 | 1.36 ± 0.43 | 5 |

TABLE 14

VIII:C in plasma from mice receiving r-VIII SQ-solution containing dextran subcutaneously. The VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.43 ± 0.43 | 6 |
| 3.5 | 1.74 ± 0.10 | 5 |
| 6 | 1.02 ± 0.51 | 5 |
| 16 | 1.54 ± 0.36 | 6 |

TABLE 15

VIII:C in plasma from mice receiving r-VIII SQ-solution containing hydrolyzed collagen subcutaneously. The VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.00 ± 0.54 | 6 |
| 7 | 1.36 ± 0.71 | 4 |
| 16 | 1.39 ± 0.93 | 6 |
| 24 | 1.31 ± 0.51 | 5 |
| 30 | 0.93 ± 0.59 | 4 |
| 48 | 1.16 ± 0.51 | 6 |

TABLE 16

VIII:C in plasma from mice receiving r-VIII SQ-solution containing a mixture of amino acids subcutaneously. The VIII:C in the administration solution was about 1,100 IU/ml. The r-VIII SQ dose was 10,000 IU/kg bodyweight.

| Time after administration (hours) | VIII:C (IU/ml) | n number of observations |
|---|---|---|
| 0 | 0.82 ± 0.43 | 12 |
| 1.5 | 1.47 ± 0.79 | 4 |
| 7 | 1.66 ± 0.21 | 4 |
| 16 | 1.26 ± 0.61 | 6 |

TABLE 17

The bioavailability of r-VIII SQ after subcutaneous administration in mice. The subcutaneously administered r-VIII SQ-solution contained varying additives in the concentration given in table 8. The VIII:C in the administration solution was about 1,100 IU/ml and the dose was 10,000 IU/kg. The bioavailability was calculated from the area under the activity (VIII:C) - time curve up to 48 h. The bioavailability after subcutaneous administration of r-VIII SQ is given in percent of the bioavailability obtained upon intravenous administration with the same dose (10,000 IU/kg).

| Additive increasing the bioavailability of factor VIII | Bioavailability (%) | Mode of administration |
|---|---|---|
| None | 100 | intravenous |
| None | 10 | subcutaneous |
| Dextran | 35 | subcutaneous |
| Hyaluronic acid | 45 | subcutaneous |
| Hydrolyzed collagen | 20 | subcutaneous |
| Hydrolyzed gelatin | 50 | subcutaneous |
| Poly (O-2-hydroxyethyl) starch | 25 | subcutaneous |
| Soybeanoil emulsion | 60 | subcutaneous |

Results

1. The results show that it is possible to increase the bioavailability of r-VIII SQ. It is also shown, that a high plasma concentration of active r-VIII SQ is obtained during a much longer period of time, up to more than 48 h, when an additive increasing the bioavailability according to the present invention is included in the subcutaneously administered formulation. This is compared to the plasma concentration obtained when a r-VIII SQ solution without such an additive is administered subcutaneously. A bioavailability of active r-VIII SQ of at least 50% is reached upon subcutaneous injection of a solution containing r-VIII SQ and hydrolyzed gelatin or soybean oil emulsion.

We claim:

1. A pharmaceutical formulation for subcutaneous, intramuscular or intradermal administration, comprising coagulation factor VIII with an activity of at least 500 IU/ml and an effective amount of organic additive to increase the bioavailability of factor VIII after subcutaneous, intramuscular or intradermal administration, which formulation is capable of increasing factor VIII activity to at least 1.5% of the normal plasma level in the blood for at least 6 hours after subcutaneous, intramuscular or intradermal administration.

2. A formulation according to claim 1, wherein the formulation is capable of providing factor VIII activity of at least 2.5% of the normal plasma level after subcutaneous, intramuscular or intradermal administration.

3. A formulation according to claim 1 wherein the factor VIII activity is capable of being maintained for at least 12 hours after subcutaneous, intramuscular or intradermal administration.

4. A formulation according to claim 1, wherein the additive is selected from the group consisting of amino acids, peptides, proteins, and combinations thereof.

5. A formulation according to claim 4, wherein the protein is selected from the group consisting of gelatin and collagen.

6. A formulation according to claim 1, wherein the additive is selected from the group consisting of polysaccharides.

7. A formulation according to claim 6, wherein the polysaccharide is selected from the group consisting of chitosans, cyclodextrins, starch, dextrans, cellulose, derivatives thereof and mixtures thereof.

8. A formulation according to claim 6, wherein the polysaccharide is selected from the group consisting of hyaluronic acids.

9. A formulation according to claim 1, wherein the additive is selected from the group consisting of oil-in-water emulsions with oil as the dispersed phase, water-in-oil emulsions with oil as the continuous phase and dispersions of polar lipids.

10. A formulation according to claim 9, wherein the oil is soybean oil.

11. A formulation according to claim 1, wherein the molecular mass of factor VIII is at least 170 kDa.

12. A formulation according to claim 1, in which the factor VIII activity is more than 1,000 IU/ml.

13. A formulation according to claim 1, having a volume of more than 0.01 ml.

14. A formulation according to claim 1, in which factor VIII is a recombinant coagulation factor VIII.

15. A formulation according to claim 14, in which factor VIII is a delection derivative of recombinant coagulation factor VIII.

16. A formulation according to claim 1, comprising:
    i) at least 500 IU/ml of factor VIII,
    ii) at least 0.01 mg/ml of polyoxyethylene sorbitan fatty acid ester,
    iii) sodium chloride,
    iv) calcium salt,
    v) an amino acid in an amount of more than 1 mM, and
    vi) the organic additive increasing the bioavailability of factor VIII.

17. A formulation according to claim 15, in which the deletion derivative factor VIII is deletion derivative recombinant factor VIII SQ (r-VIII SQ).

18. A formulation according to claim 1, which is a stable aqueous solution or dispersion ready for administration.

19. A mixture comprising a formulation according to claim 18, mixed with one or more aqueous solutions or dispersions.

20. A formulation according to claim 1, which is dried and capable of reconstitution with one or more aqueous solutions or dispersions before administration.

21. A method for treating hemophilia comprising subcutaneously, intramuscularly or intradermally administering a formulation according to claim 1.

22. A formulation according to claim 2, wherein the additive is selected from the group consisting of amino acids, peptides, proteins, and combinations thereof.

23. A formulation according to claim 2, wherein the additive is selected from the group consisting of polysaccharides.

24. A formulation according to claim 23, wherein the polysaccharide is selected from the group consisting of hyaluronic acids.

25. A formulation according to claim 1, wherein the factor VIII activity is more than 1,500 IU/ml.

26. A formulation according to claim 1, having a volume of from 0.1 to 2 ml.

27. A formulation according to claim 1, comprising:
    i) at least 1,500 IU/ml of a deletion derivative of a recombinant factor VIII,
    ii) at least 0.01 mg/ml of polyoxyethylene sorbitan fatty acid ester,
    iii) sodium chloride in an amount of more than 0.1M,
    iv) calcium chloride or calcium gluconate in an amount of more than 0.5 mM,
    v) L-histidine in an amount of more than 1 mM, and
    vi) the organic additive increasing the bioavailability of factor VIII.

28. A formulation according to claim 1, wherein the additive comprises safflower oil.

29. A formulation according to claim 1, wherein the additive comprises a polar lipid.

30. A formulation according to claim 29, wherein the polar lipid comprises phospholipid or glycolipid.

* * * * *